(12) United States Patent
D'urso et al.

(10) Patent No.: US 8,540,155 B2
(45) Date of Patent: Sep. 24, 2013

(54) AIMING ASSISTANCE FOR SPORT COMPETITIONS FOR VISUALLY CHALLENGED OR BLIND PERSONS

(75) Inventors: Guy D'urso, Houilles (FR); Jean-Marie Henault, Magny les Hemeaux (FR); Jocelyn Chanussot, Grenoble (FR); Vincent Couturier-Doux, La Tronche (FR)

(73) Assignee: Electricite de France, Paris (FR)

( * ) Notice: Subject to any disclaimer, the term of this patent is extended or adjusted under 35 U.S.C. 154(b) by 0 days.

(21) Appl. No.: 13/376,659

(22) PCT Filed: Jun. 3, 2010

(86) PCT No.: PCT/FR2010/051092
§ 371 (c)(1),
(2), (4) Date: Dec. 7, 2011

(87) PCT Pub. No.: WO2010/142891
PCT Pub. Date: Dec. 16, 2010

(65) Prior Publication Data
US 2012/0080523 A1    Apr. 5, 2012

(30) Foreign Application Priority Data
Jun. 10, 2009  (FR) ..................................... 09 53846

(51) Int. Cl.
*G06F 19/00*  (2011.01)

(52) U.S. Cl.
USPC ............................ 235/404; 235/405; 235/406

(58) Field of Classification Search
USPC ........................................ 235/404, 405, 406
See application file for complete search history.

(56) References Cited

FOREIGN PATENT DOCUMENTS

| | | |
|---|---|---|
| DE | 102 53 646 A1 | 6/2004 |
| DE | 103 60 716 A1 | 7/2005 |
| WO | WO 83/00919 A1 | 3/1983 |
| WO | WO 01/38823 A1 | 5/2001 |

*Primary Examiner* — Karl D Frech
(74) *Attorney, Agent, or Firm* — Drinker Biddle & Reath LLP

(57) ABSTRACT

An automated aiming assistance towards a shooting target for a visually- challenged or blind person is provided. The method comprises: providing the shooting weapon used by the person with a camera placed on the weapon for filming the target to be aimed at; identifying the target by shape recognition in the images shot by the camera; and transmitting a signal received by the person for guiding the person for orienting the shooting weapon towards the target.

12 Claims, 3 Drawing Sheets

DD... Device (INVENTION)

DD... Device

US 8,540,155 B2

AIMING ASSISTANCE FOR SPORT COMPETITIONS FOR VISUALLY CHALLENGED OR BLIND PERSONS

CROSS-REFERENCE TO RELATED APPLICATIONS

This application is the U.S. national phase of the International Patent Application No. PCT/FR2010/051092 filed Jun. 3, 2010, which claims the benefit of French Application No. 09 53846 filed Jun. 10, 2009, the entire content of which is incorporated herein by reference.

FIELD OF THE INVENTION

The invention relates to automated assistance for visually-challenged persons (blind or with poor vision) for aiming at archery or rifle targets in the context of sport competitions.

BACKGROUND

A prior art aiming assistance system offered by the German company Swarovsky is represented in FIG. 1. It comprises a circular grayscale target pattern MI (the grayscales darkening from white to black from the center of the target to the edge), placed just above the target CI. The target pattern is brightly lit by a light placed just above it, and at the focal point of the scope LU mounted on the weapon AR there is a light intensity sensor (typically a monopixel detector). When the center of the target pattern MI is imaged on this detector, the light intensity is at its maximum, and an acoustic signal is sent to the shooter to indicate that his weapon is aiming at the center of the target CI. One will note that the scope LU is pre-oriented to the angle a formed by the axis passing through the scope LU and the target pattern MI, relative to the aiming axis (from the weapon AR to the center of the target CI).

Adjusting the position of the target pattern MI relative to the target must be done with precision, so that the same value of the angle a is defined and the shooter always has his weapon facing the center of the target. In addition, the position of the target pattern MI relative to the target CI must be adjusted each time to the position of the shooter (according to his distance to the target (200, 100, or 50 meters), whether he is standing, crouched, or lying down, etc.).

Such a system is therefore fairly difficult to use and is impractical for competitions.

In addition, a "tilt" problem occurs if the shooter does not maintain the same exact position when shooting. This type of system communicates to the shooter an aiming direction which is offset from what the system is truly trying to detect (the target pattern MI in this case), and due to the initial alignment of the weapon to a point which is not the center of the target CI, it has been observed than a tilt angle a disrupts the quality of the shot.

Targets for competitive shooting generally have officially defined characteristics and therefore do not vary in shape and/or color, whether they are intended for use by persons with or without disabilities. There is no question of changing the appearance of the targets to adapt them to existing aiming-assistance systems.

SUMMARY

The present invention improves the situation.

It first proposes a method, implemented by computerized means, to assist a visually challenged or blind person with aiming at a shooting target, comprising:

providing the shooting weapon to be used by the person with a camera placed on the weapon to capture images of the target to be aimed at,
identifying the target by shape recognition in the images captured by the camera,
emitting a signal to be perceived by the person to guide the person in orienting the shooting weapon towards the target.

By seeking to recognize the target itself, using shape recognition in advantageous embodiments which will be described below, it is no longer necessary to install an additional target pattern and no tilt angle interferes with the quality of the shot. The characteristics of the target itself are used to recognize and locate its center.

In an advantageous embodiment, after the target is identified in the captured images, the center of the target is determined and the emitting of the signal guides the person in orienting the weapon, particularly towards the center of the target.

This advantageous embodiment is based on the fact that the target displays a circle, disk, or ring (at least one), as do most shooting targets as will be discussed below with reference to FIGS. 4A and 4B. In an advantageous embodiment, the shape recognition in the sense of the invention comprises a Hough transformation to identify such a shape in the captured images, and from that, the center of this circular shape.

More specifically, if the target has a plurality of shapes forming at least one concentric circle, ring, or disk, the Hough transformation allows identifying, among this plurality of circular shapes, at least two shapes having respective centers that are separated by a distance of less than a chosen tolerance threshold. If these two shapes can be identified, it can be decided that the center of the target is the barycenter of the centers of the two circular shapes.

Advantageously, there is a confirmation of the identification of the target obtained by the shape recognition as described above.

In one embodiment, the color of the target is made use of to confirm the shape recognition. For example, one can use recognition of a color contrast between different rings of a particular color, such as the rings of an archery target. Additionally or alternatively, two shape recognitions can be carried out:
a first shape recognition in grayscale images, and
a second shape recognition, using color, performed on color images and using a selected color component (green for example in a RGB (Red Green Blue) image).

The second shape recognition confirms the result of the first grayscale shape recognition, but in the color image.

As an alternative or addition to the types of shape recognition described above, because a rectangular board is generally used to support the shooting target, the shape recognition of the invention can comprise the identification of four corners having angles close to 90° and spaced apart by predetermined relative distances (for example by the same relative distance if it is a square, as will be further described below).

One particular embodiment can consist of:
applying a first shape recognition comprising a Hough transformation, and
confirming the obtained results by a second shape recognition based on the identification of four corners.

In a practical embodiment of the invention, a processing module can be connected to the camera, by means of which:
selected shape characteristics of a target model are stored in memory,
data for the current image are received from the camera, the current image data are examined for shape characteristics which are homologous to the model characteristics (for example a given number of concentric circles, four corners with predetermined distance ratios between corners, or other characteristics), and if characteristics identical to the model characteristics are identified in the current image data, within a certain tolerance (this tolerance for example taking into account perspective effects, differences in color temperature from the lighting, distance between camera and target, or other effects):

the recognition of the target in the current image is validated, a distance is determined between the target and a center of aim of the camera, and an output signal is issued for which at least one parameter is a function of this distance.

In practice, a signal is delivered which is a function of:

the distance in height (angle of elevation to be corrected for the shooter), and the horizontal distance to the target (angle of azimuth to be corrected for the shooter).

One can then choose an acoustic output signal and modulate this signal with at least one parameter from among an amplitude, an amplitude of spatialization (between the right earpiece and the left earpiece of a headset, for example), a fundamental frequency, and a modulation frequency (in the form for example of beeps that are closer together or further apart), as a function of the above distance.

The invention also relates to a system to assist with aiming at a shooting target, which applies the above method and comprises:

a camera to be placed on a weapon to be used by the person, to capture images of a target, a device connected to the camera, for identifying the target by shape recognition in the images captured by the camera, and a means, for example a stereophonic headset or an earpiece, connected to the device, for emitting a signal to be perceived by the person to guide the person in orienting the shooting weapon towards the target.

BRIEF DESCRIPTION OF THE DRAWINGS

Other features and advantages of the invention will be apparent from reading the following detailed description and the attached drawings in which, aside from the previously described FIG. 1 which concerns the prior art.

DETAILED DESCRIPTION

Figure 1:
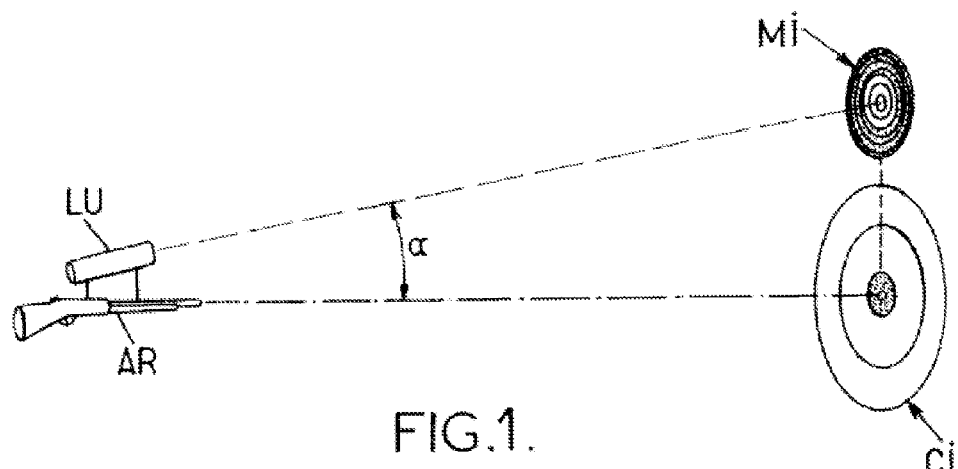
Figure 2:
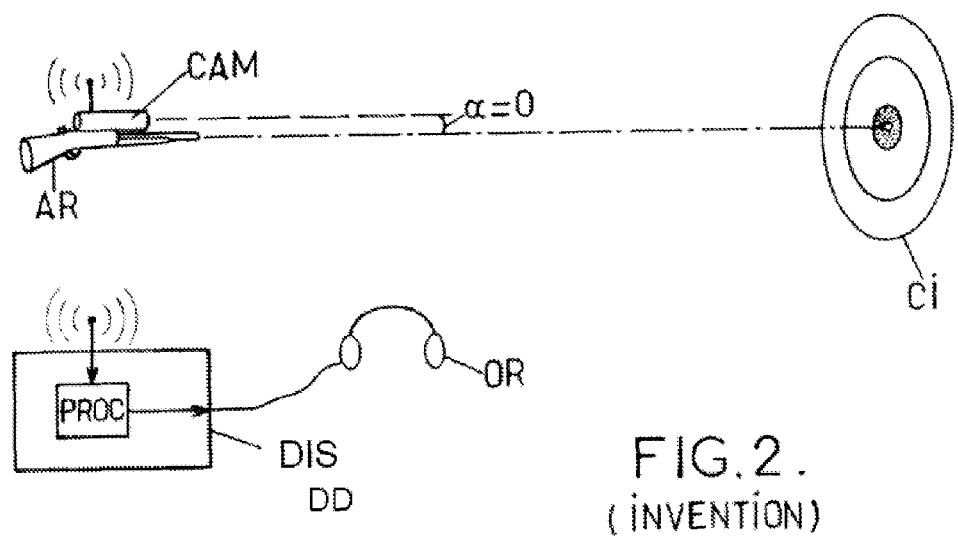
FIG. 2 schematically illustrates a system of the invention, assembled on a weapon.

As illustrated in FIG. 2, an aiming assistance system of the invention comprises a camera CAM capturing images of the target CI in order to identify the target by shape recognition when the weapon (bow, rifle, dart, or other weapon) is pointed towards the target. When the complete shape of the target is recognized by the camera using a zoom adjusted to the assumed distance of the target, an audible signal sounds in the earpieces OR worn by the person to be assisted, to indicate to him that the weapon AR is pointed towards the target.

In an exemplary embodiment, the camera CAM can send a video signal by a wired or wireless link (Wifi or other) to a device DIS that the shooter can wear (for example in a backpack or by other means). The advantage of such an implementation is that it limits the weight mounted onto the weapon to the weight of the camera only, because the heavier the weapon the greater the inaccuracy of the shooter due to muscle fatigue.

A processor PROC equipped with working memory receives video data, defines an image, and compares the shape of this image with a presaved model (or more specifically as will be seen below, compares certain characteristics of this image to those of the model). In an exemplary embodiment described in detail below, the shape recognition is based on a Hough transformation. This type of processing is well suited for the recognition of circular shapes. Circle recognition by Hough transformation generally consists of the following steps identifying substantially uniform contrasting areas in an image (for example an area where the grayscale is constant within a certain tolerance), defining tangents to this area, determining the normals to the tangents, and verifying that they are (almost) all secant (within a certain tolerance) at a point which is the center of a circle or disk formed by the area.

This circle detection, as well as a square detection for identifying the physical edges of the target, will be detailed below.

The earpieces OR can be in the form of a headset with small speakers for the right and left ears. The angle of elevation for the aim can be adjusted by varying the tone relative to a reference frequency. Thus the speakers can reproduce:

a first signal varying in frequencies and depending on the height of the aiming axis relative to the target, and a reference second signal of constant frequency.

This second signal can be reproduced at a sound level that is equal between the two speakers, so that the shooter has the sensation that this reference signal is centered between his two ears. The first signal can be reproduced at a sound level which varies between the two speakers as a function of the angle of azimuth of the aiming axis relative to the target. When the shooter has the impression of hearing the two signals completely "superimposed" as he moves his weapon, the aiming axis passes through the center of the target and the user can shoot.

As a variant, to assist with adjusting the angle of azimuth, the first signal can consist of emitting beeps at a frequency which increases as the aiming axis approaches the target horizontally, until a continuous signal is heard, in which case the user can fire. One will note that a stereophonic headset is not necessary in this variant and a single earpiece is sufficient.

In a less sophisticated variant which still provides good results, the first signal consists of emitting beeps at a frequency which increases as the aiming axis approaches the target for the angles of azimuth and elevation indistinguishably, until a continuous signal is reached, in which case the user can fire. In this embodiment, reproducing a reference signal is unnecessary and a single earpiece is sufficient.

However, a difficulty arises in implementing the invention, particularly in outdoor or hazy conditions: increasing the tolerance for the target detection in such conditions (with variations in the natural lighting on the target, possibly with slight haze or mist, etc.) allows better detection of the target but leads to a risk of false positives in the detection, which is of course hazardous in a context of weapon use.

An advantageous embodiment proposes combining the shape recognition described above with recognition based on the color of certain target elements and/or on square recognition, as described below.

In archery, the targets have an outside diameter of 122 cm and consist of concentric circles of colors in the sequence, from the outside to the inside, of white, black, blue, red, and yellow, on a white background.

In riflery, the targets have an outside diameter of 155 mm and consist of ten concentric circles on a white background with a central mark (three black concentric disks) 59.5 mm in diameter, on cardboard that is 170 mm per side.

Figure 3:
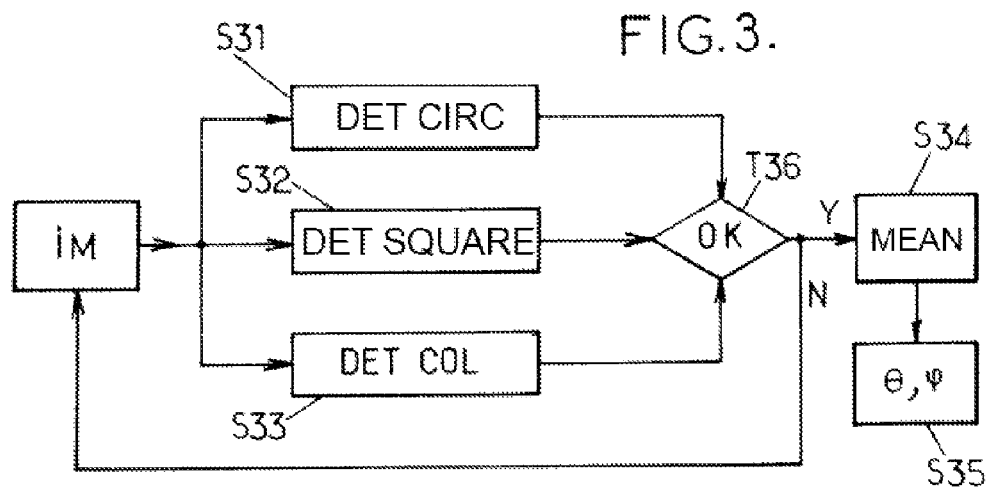
FIG. 3 illustrates the general steps of a method of the aiming assistance invention.

In both cases, the target and its center are detected by processing images as illustrated in FIG. 3. The processing first consists of grayscale circle detection (step S31) in a current image IM. The circles correspond:
 for archery, to the various concentric circles on the target of different colors, and
 for riflery, to the black central mark.

The circle detection is advantageously based on using the Hough transform, which corresponds to determining the intersection of lines perpendicular to the contours as explained above. The points of the image having a large number of line intersections are the centers of the circles. The Hough transform is classic and can be found in the libraries of traditional computerized tools.

In particular, grayscale circle detection comprises the following operations, in an exemplary embodiment:
 converting the color image into grayscale,
 applying a Gaussian filter (for example 9 pixels by 9) to reduce noise and decrease false detections, and
 applying the Hough transform while retaining only the first circle detected (typically the circle having the center with the largest number of intersections).

The processing can additionally comprise, for example, square detection, particularly the outside edges of the target board. This detection (step S32) is based on the use of specific processing defined as follows:
 detecting boundaries in the image,
 selecting boundaries using the following criteria:
  there are four and only four sides to be identified,
  the boundary line is closed,
  the angle formed by two consecutive sides must be 90° (within a certain tolerance due to a slight possible perspective effect, depending on the position of the shooter),
  the area within the boundary must be between two thresholds (min and max),
  the ratio between the largest side and the smallest side must be close to one, within a certain tolerance.

In the example represented in FIG. 3, several criteria are used to detect a shooting target:
 detection of a circle in a grayscale image (step S31),
 detection of squares (step S32), and
 detection of a circle in an image corresponding to a component in the color space (step S33).

When selecting the color used for the third detection, detecting the "Green" component of the RGB (Red Green Blue) color space has been found to be the most relevant in competition conditions. The main steps of this detection are as follows:
 selecting the Green component (for example green pixels within a certain tolerance) in the color image,
 applying a Gaussian filter (for example 9×3) to reduce noise and decrease false detections, and
 applying the Hough transform with only the first detected circle retained (circle having the center with the largest number of intersections).

One can see that the circle detection is repeated independently of the grayscale circle processing done in the previous step S31.

Thus for a current image IM:
 circle detection is performed in the grayscale image (S31),
 for the same image, square detection is performed (S32),
 for the same image, circle detection is performed in the color image (S33).

Then the coordinates (x,y for a two-dimensional image) are determined:
 for the center of a first circle obtained in step S31,
 for the center of a square obtained in step S32,
 and for the center of a second circle obtained in step S33.

These coordinates are considered to be validated if the distance between the centers, taken two by two, is always less than a given threshold (near 0). Otherwise the detections are rejected (the arrow N from the test T36 in FIG. 3) and the detections are repeated on a new current image. No acoustic signal is emitted for the shooter as long as the coordinates of the detected centers have not been validated.

If the detections are positive, the barycenter of the validated centers is considered to be the center of the target in step S34. By comparing the position of this barycenter with that of the central area of the image (for example the 9×9 pixels in the center of the image):
 the difference in pixels along the vertical axis y is calculated and a corresponding acoustic signal is emitted for the shooter (for example at a frequency dependent on this difference taken as a positive or negative value), to indicate a deviation in the angle of elevation $\phi$ component of the aim, and
 the difference in pixels along the horizontal axis x is calculated and a corresponding acoustic signal is emitted for the shooter (for example with a difference in intensity in the speakers of his stereophonic headset which is dependent on this difference taken as a positive or negative value), to indicate a deviation in the angle of azimuth $\theta$ component of the aim.

Combining two of the three detections presented above has been found to be sufficient to ensure that the target has been properly located, without false positives.

However, tests have found that the combined detection of grayscale circles and squares did reduce false positives but had the result of increasing the processing time, which adversely impacts shooting accuracy because the shooter is moving during this processing time.

Using the two circle detections S31 and S33 (one using a grayscale image, and the other using the same image in color), both based on a Hough transformation, yields good results for both the reliability of the detection and the processing in real time, with the sound heard by the shooter perceived as being instantaneous in response to his movements.

Figure 4A:
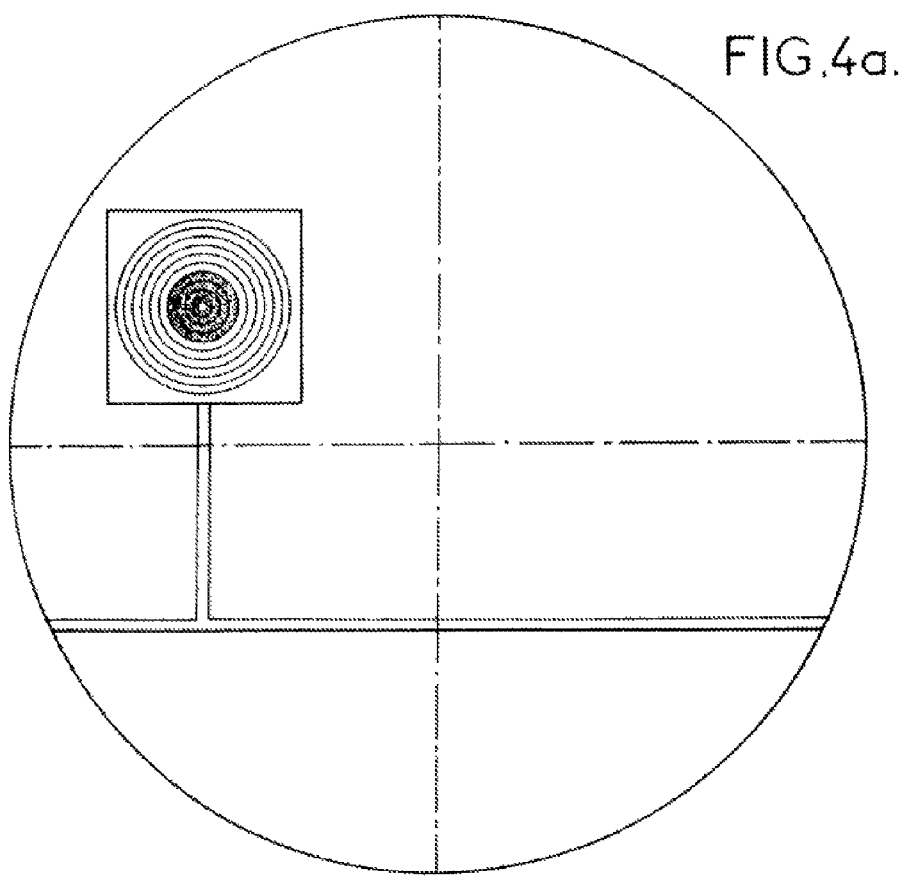
FIGS. 4A and 4B are target images captured with a camera in two distinct focal length configurations, and FIG. 5 schematically represents a device according to the invention for processing image data provided by the camera, determining the presence or absence of the target in the images provided, and in particular identifying the center of the target if applicable.

Another parameter to be optimized is the adjustment of the focal length (zoom) of the camera relative to the distance between the shooter and the target. To ensure accurate detection of the center of the target in the image, the dimensions of the target in the current image preferably must be as large as possible without falling outside the edges of the image. The corners of the target should then more or less coincide with the edges of the image (as represented in the view in FIG. 4B of an official archery target). However, for the sound indicators to be effective for the shooter, the image must encompass the target as well as its surroundings. In other words, for the camera to be able to capture the target in its field with the shooter then alerted to limit the amplitude of his movements, the image captured by the camera must typically have a width of three to five seven times that of the target (as represented in the view in FIG. 4A of an official target for pistol shooting at 10 meters).

Of course, depending on the means available and particularly the pixel resolution of the camera, a more or less powerful zoom can be chosen (less zoom when the camera resolution is high).

To use a weapon equipped with the same camera, of a given resolution, in several types of competition, it is therefore advantageous to preadjust the zoom of the camera according to:
 the target size, and
 the target distance
for each type of competition.

Of course, the invention is not limited to the embodiment described above as an example; it extends to other variants.

For example, it is understood that the choice of the color green for the shape recognition confirmation conducted in the color image can vary with the implementation conditions and particularly the lighting conditions on the target (in a shooting gallery or outdoors for example).

Figure 4B:
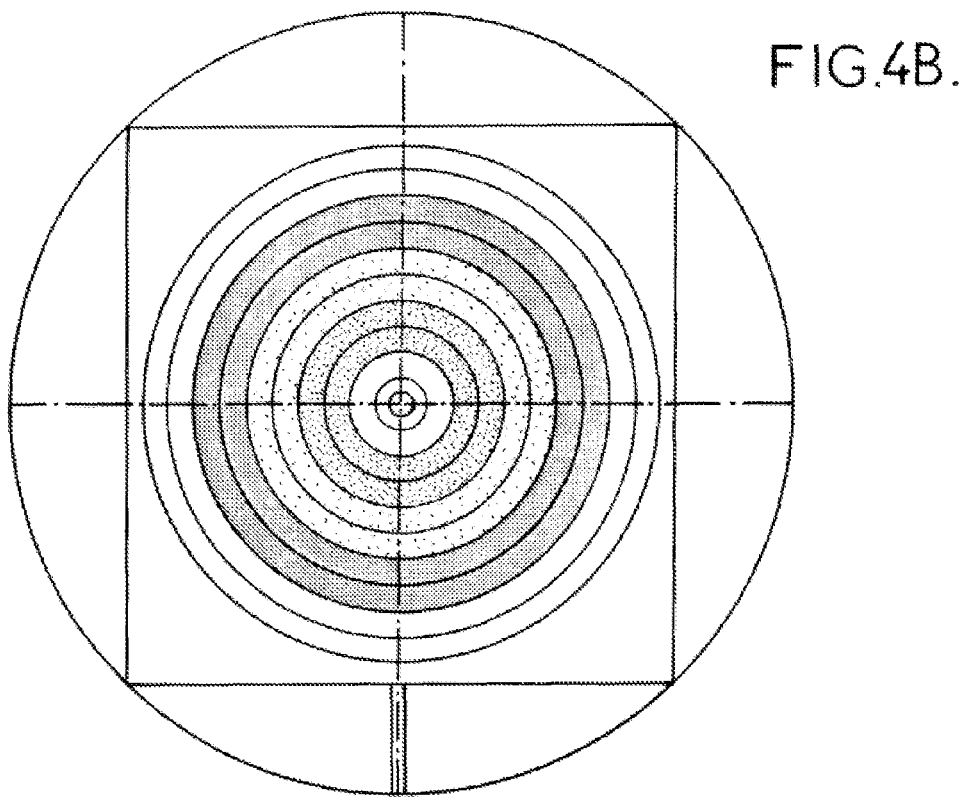

The use of color in the obtained images can imply shape recognition in a given color (green for example), but also a recognition of color contrasts in the target. This embodiment is particularly applicable in the case of an archery target, where it is possible to rely on recognition of the colors of the different concentric rings to confirm the grayscale shape recognition (FIG. 4B).

Figure 5:
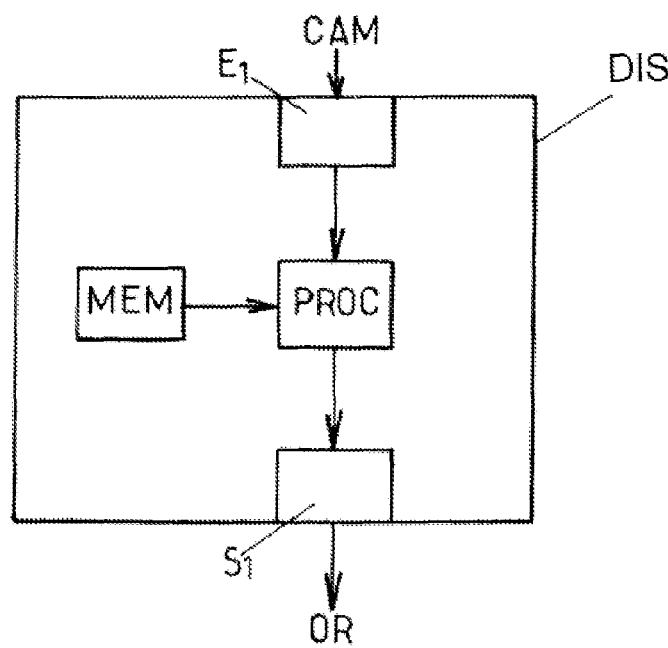

With reference to FIG. 5, the invention also relates to a device DIS of a system to assist a visually challenged or blind person with aiming at a shooting target, comprising:
 a memory MEM for storing the selected shape characteristics of a target model,
 an input E1 for receiving current image data from the camera CAM, and
 a processor PROC for:
  searching the current image data for shape characteristics that are homologous to the model characteristics, and
  if characteristics identical to the model characteristics are identified in the current image data, within a certain tolerance:
   deciding that the target has been recognized in the current image,
   determining a distance between the target and a center of aim of the camera,
 and an output S1 for delivering a signal for which at least one parameter is a function of this distance.

The invention also relates to a computer program to be stored in the memory of such a device and comprising instructions for carrying out the method of the invention, when they are executed by the processor PROC of the device. As an example, FIG. 3 can represent a flow chart for such a computer program.

The invention claimed is:

1. A method to assist a visually challenged or blind person with aiming at a shooting target, comprising:
 providing the shooting weapon to be used by the person with a camera placed on the weapon to capture images of the target to be aimed at,
 identifying the target by shape recognition in the images captured by the camera, emitting a signal to be perceived by the person to guide the person in orienting the shooting weapon towards the target
 wherein the target displays at least one shape which forms a circle, disk, or ring, and wherein the shape recognition comprises a Hough transformation to identify said shape in the captured images.

2. The method according to claim 1, wherein, after the target is identified in the captured images, the center of the target is determined and the emitting of the signal guides the person in orienting the shooting weapon towards the center of the target.

3. The method according to claim 1, wherein the target displays a plurality of shapes which form at least one concentric circle, ring, or disk, and wherein the Hough transformation identifies among said plurality of shapes at least two shapes having respective centers separated by a distance of less than a chosen tolerance threshold.

4. The method according to claim 1, wherein said target is colored and wherein processing is applied which uses the color of the target to confirm the shape recognition.

5. The method according to claim 4, wherein at least the following are applied:
 a first shape recognition, to the images as grayscale images, and
 a second shape recognition, to the images as color images, using a selected color component.

6. The method according to claim 1, wherein a rectangular board comprises the target to be aimed at, and wherein the shape recognition comprises the identification of four corners having angles close to 90° and spaced apart by predetermined relative distances.

7. The method according to claim 1, wherein at least the following are applied:
 a first shape recognition comprising a Hough transformation, and
 a second shape recognition based on the identification of four corners.

8. The method according to claim 1, wherein:
 selected shape characteristics of a target model are stored in memory,
 data for the current image are received from the camera,
 the current image data are examined for shape characteristics which are homologous to the model characteristics, and
 if characteristics identical to the model characteristics are identified in the current image data, within a certain tolerance:
  the target is recognized in the current image ,
  a distance is determined between the target and a center of aim of the camera, and
  an output signal is issued for which at least one parameter is a function of said distance.

9. The method according to claim 8, wherein the output signal is acoustic and said parameter is chosen from among an amplitude, an amplitude of spatialization, a fundamental frequency, and a modulation frequency, as a function of said distance.

10. A non-tangible computer readable medium comprising a program comprising instructions for carrying out the method according to claim 1, when they are executed by a processor of a device of a system to assist a virtually challenged or blind person with aiming at a shooting target.

11. A system to assist a visually challenged or blind person with aiming at a shooting target, the system comprising:
 a camera to be placed on a weapon to be used by the person, to capture images of a target, a device connected to the camera, for identifying the target by shape recognition in images captured by the camera, and a means connected to the module for emitting a signal to be perceived by the person to guide the person in orienting the shooting weapon towards the target.

12. A device of a system to assist a visually challenged or blind person with aiming at a shooting target, comprising:

a memory for storing the selected shape characteristics of a target model, an input for receiving current image data from a camera, and a processor for searching the current image data for shape characteristics that are homologous to the model characteristics, and if characteristics identical to the model characteristics are identified in the current image data, within a certain tolerance:

deciding that the target is recognized in the current image, determining a distance between the target and a center of aim of the camera, and an output for delivering a signal for which at least one parameter is a function of said distance.

* * * * *